United States Patent
Lai

(10) Patent No.: US 7,252,505 B2
(45) Date of Patent: *Aug. 7, 2007

(54) SELF-LIGATING ORTHODONTIC APPLIANCE WITH POST FOR CONNECTION TO A LATCH

(75) Inventor: Ming-Lai Lai, Arcadia, CA (US)

(73) Assignee: 3M Innovative Properties Company, St. Paul, MN (US)

( * ) Notice: Subject to any disclaimer, the term of this patent is extended or adjusted under 35 U.S.C. 154(b) by 299 days.

This patent is subject to a terminal disclaimer.

(21) Appl. No.: 10/900,888

(22) Filed: Jul. 28, 2004

(65) Prior Publication Data

US 2006/0024635 A1 Feb. 2, 2006

(51) Int. Cl.
*A61C 3/00* (2006.01)

(52) U.S. Cl. .................................................. 433/11

(58) Field of Classification Search ............. 433/8–11, 433/13–14, 22
See application file for complete search history.

(56) References Cited

U.S. PATENT DOCUMENTS

| | | | |
|---|---|---|---|
| 1,991,047 A * | 2/1935 | Boyd et al. .................. 433/11 |
| 3,327,393 A * | 6/1967 | Brader ......................... 433/11 |
| 3,930,311 A | 1/1976 | Andrews |
| 4,496,318 A | 1/1985 | Connelly, Jr. |
| 5,269,681 A | 12/1993 | Degnan |
| 5,358,402 A | 10/1994 | Reed et al. |
| 5,366,372 A | 11/1994 | Hansen et al. |
| 5,380,196 A | 1/1995 | Kelly et al. |
| 5,439,379 A | 8/1995 | Hansen |
| 5,516,284 A | 5/1996 | Wildman |
| 5,711,666 A | 1/1998 | Hanson |
| 5,971,753 A | 10/1999 | Heiser |
| 6,302,688 B1 | 10/2001 | Jordan et al. |
| 6,394,798 B1 | 5/2002 | Huff et al. |
| 6,554,612 B2 | 4/2003 | Georgakis |
| 6,582,226 B2 | 6/2003 | Jordan et al. |
| 2004/0086825 A1 | 5/2004 | Lai et al. |
| 2004/0086826 A1 | 5/2004 | Pospisil |

FOREIGN PATENT DOCUMENTS

WO WO 2005/060861 7/2005

OTHER PUBLICATIONS

Pending U.S. Appl. No. 10/730,344, filed Dec. 8, 2003; Ceramic Orthodontic Appliance With Archwire Slot Liner.
Pending U.S. Appl. No. 10/698,285, filed Oct. 31, 2003; Orthodontic Appliance With Latch for Retaining an Archwire.

* cited by examiner

*Primary Examiner*—John J Wilson
(74) *Attorney, Agent, or Firm*—James D. Christoff

(57) ABSTRACT

An orthodontic appliance includes a latch that comprises at least one clip with a region for receiving an archwire. The clip also includes a recess for receiving a post of the appliance and for coupling the clip to remaining components of the appliance. The post includes a neck and an outermost head, and the neck and the head are constructed to reduce the extent that the clip must be opened to fit the clip over the head and onto the post during assembly of the appliance.

10 Claims, 4 Drawing Sheets

SELF-LIGATING ORTHODONTIC APPLIANCE WITH POST FOR CONNECTION TO A LATCH

BACKGROUND OF THE INVENTION

1. Field of the Invention

This invention broadly relates to appliances that are used in the course of orthodontic treatment. More particularly, the present invention relates to a self-ligating orthodontic appliance such as a bracket or molar appliance having a latch that releasably retains an archwire in an archwire slot of the appliance.

2. Description of the Related Art

Orthodontic therapy is a specialized type of treatment within the field of dentistry, and involves movement of malpositioned teeth to orthodontically correct locations. Orthodontic treatment typically enhances the aesthetic appearance of the teeth, particularly in instances when the patient's front teeth are malpositioned or crooked. Orthodontic treatment can also improve the patient's occlusion so that the teeth function better with each other during mastication.

Many types of orthodontic treatment programs involve the use of a set of tiny appliances and wires that are commonly known collectively as "braces". During such treatment programs, small slotted appliances known as brackets are fixed to the patient's anterior, cuspid and bicuspid teeth, and an archwire is inserted into the slot of each bracket. The archwire forms a track to guide movement of the teeth to orthodontically correct locations. End sections of the archwires are typically captured in molar appliances that are fixed to the patient's molar teeth.

Recently, there has been increased interest in orthodontic appliances that have a latch for retaining the archwire in the archwire slot. Appliances of this type are widely known as self-ligating appliances and often obviate the need to use ligatures (such as wire ties or elastomeric O-rings) for retaining the archwire in the archwire slots. Improved self-ligating orthodontic appliances having a self-releasing latch are described in applicant's U.S. Pat. Nos. 6,302,688 and 6,582,226.

A recently introduced self-ligating appliance known as "SMARTCLIP" brand appliance from 3M Unitek Corporation has a latch that comprises two resilient clips, and each clip has a generally "C"-shaped configuration. The clips spread open to admit an archwire into an archwire slot of the appliance. Each clip is connected to a body of the appliance by a post that extends through the clip. Each post has a neck and an enlarged head for retaining the clip, and the neck and the head both have semicircular shapes with common points of origin when viewed in directions toward the sides of the appliance.

SUMMARY OF THE INVENTION

The present invention is directed toward a self-ligating orthodontic appliance having at least one post for coupling a latch to remaining components of the appliance. The latch includes at least one clip having a recess, and the post extends into the recess. The post includes an outermost head and a neck that connects the head to the appliance body, and the head and neck are constructed to facilitate attachment of the clip to the post during manufacture of the appliance.

In more detail, the present invention is directed in one aspect to an orthodontic appliance that comprises a base, a body extending outwardly from the base and an archwire slot extending across the appliance in a generally mesial-distal direction. The appliance also includes a latch for releasably retaining an archwire in the archwire slot. The latch comprises a clip with a region next to the archwire slot for receiving an archwire, and the clip also includes a recess and a section extending next to the recess. The appliance further comprises a post extending outwardly from the body along a reference axis and into the recess for coupling the clip to the body. The post includes an outermost head and a neck interconnecting the head and body. The head extends outwardly past the neck a certain distance when considered in reference planes perpendicular to the reference axis, and the certain distance decreases as the section of the clip is approached.

Another aspect of the present invention is also directed to an orthodontic appliance that comprises a base, a body extending outwardly from the base and an archwire slot extending across the appliance in a generally mesial-distal direction. The appliance also comprises a latch for releasably retaining an archwire in the archwire slot. The latch comprises a clip with a region next to the archwire slot for receiving an archwire, and the clip includes a recess and a section extending next to the recess. The appliance further comprises a post extending outwardly from the body along a reference axis and into the recess for coupling the clip to the body. The post includes an outermost head and a neck interconnecting the head and the body. The head has a certain height when considered along reference axes that extend in an occlusal-gingival direction, and the certain height decreases as the section is approached.

The present invention is directed in another aspect to an orthodontic appliance that comprises a base, a body extending outwardly from the base and an archwire slot extending across the appliance in a generally mesial-distal direction. The appliance also includes a latch for releasably retaining an archwire in the archwire slot, wherein the latch comprises a clip with a region next to the archwire slot for receiving an archwire. The clip includes a first section, a second section and a third section interconnecting the first section and the second section, and the clip also includes a recess at least partially defined by the first section, the second section and the third section. The appliance further comprises a post extending outwardly from the body along a reference axis and into the recess for coupling the clip to the body. The post includes an outermost head and a neck interconnecting the head and the body. The head extends outwardly past the neck a certain distance when considered in reference planes perpendicular to the reference axis, and the certain distance decreases as the third section of the clip is approached.

The present invention is a significant advantage during assembly of the appliance, since the clip can be spread open and placed over the head of the post by moving the clip in a lateral direction toward the archwire slot. The construction of the post as described in the various embodiments reduces the need to spread open the clip during assembly to a substantial extent. As a consequence, the amount of stress that might otherwise be imposed on the clip when the clip is spread open is reduced, helping to ensure that the fatigue life of the clip is not unduly compromised.

Additional aspects and features of the invention are set out in the detailed description that follows and are illustrated in the accompanying drawings.

DEFINITIONS

Figure 1:
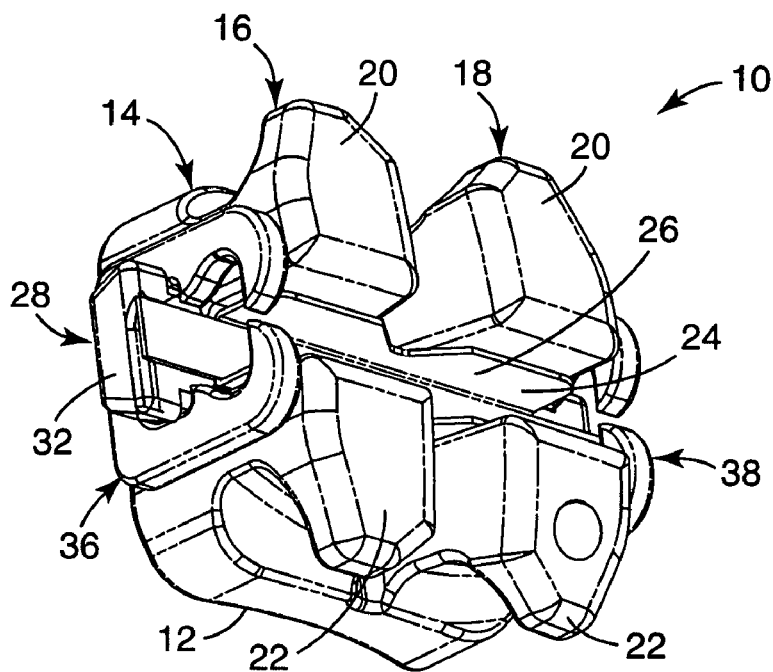
FIG. 1 is a perspective view of an orthodontic appliance constructed in accordance with one embodiment of the present invention, looking at the appliance toward its mesial, buccolabial and gingival sides.

"Mesial" means in a direction toward the center of the patient's curved dental arch.

"Distal" means in a direction away from the center of the patient's curved dental arch.

"Occlusal" means in a direction toward the outer tips of the patient's teeth.

"Gingival" means in a direction toward the patient's gums or gingiva.

"Buccolabial" means in a direction toward the patient's lips or cheeks.

"Lingual" means in a direction toward the patient's tongue.

DETAILED DESCRIPTION OF THE PREFERRED EMBODIMENTS

An orthodontic appliance constructed in accordance with one embodiment of the present invention is illustrated in FIGS. 1-8 and is broadly designated by the numeral 10. The appliance 10 in this instance is an orthodontic bracket that is adapted to be secured to an enamel surface of a patient's tooth, such as a buccolabial tooth surface. Alternatively, the appliance could be a molar appliance, an appliance for attachment to a lingual tooth surface, or any other appliance that is adapted to receive an archwire for controlling movement of the associated tooth during the course of orthodontic therapy.

The appliance 10 includes a base 12 for bonding the appliance 10 directly to the patient's tooth enamel by the use of an adhesive. Preferably, the base 12 has an outwardly facing concave compound contour that matches the convex compound contour of the patient's tooth surface to which it is bonded. Optionally, the base 12 is provided with grooves, particles, recesses, undercuts, a chemical bond enhancement material or any other material or structure, or any combination of the foregoing that facilitates bonding of the appliance 10 directly to the patient's tooth surface.

A body 14 extends outwardly from the base 12 in a generally buccolabial direction. The body 14 includes a mesial body portion 16 and a distal body portion 18 that is spaced from the mesial body portion 16. In this embodiment, each of the portions 16, 18 includes an occlusal tiewing 20 and a gingival tiewing 22, although one or more of the tiewings 20, 22 could be omitted if desired.

Figure 2:
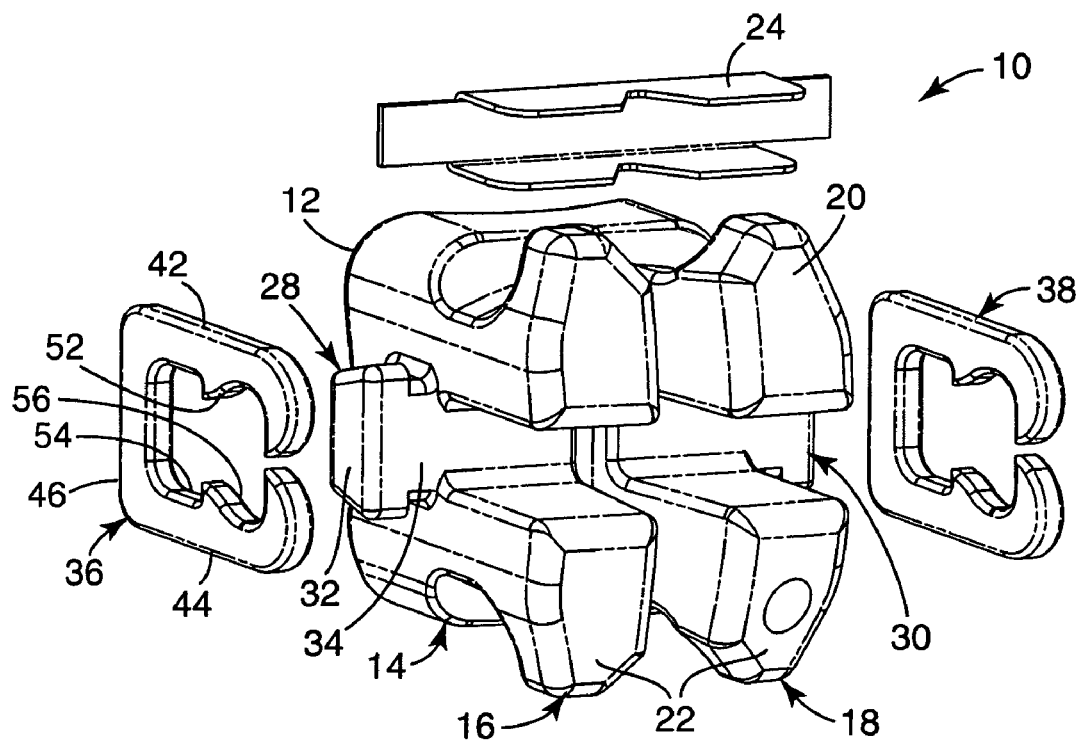
FIG. 2 is an exploded perspective view of the appliance depicted in FIG. 1, looking at the appliance toward its mesial, buccolabial and occlusal sides.
Figure 3:
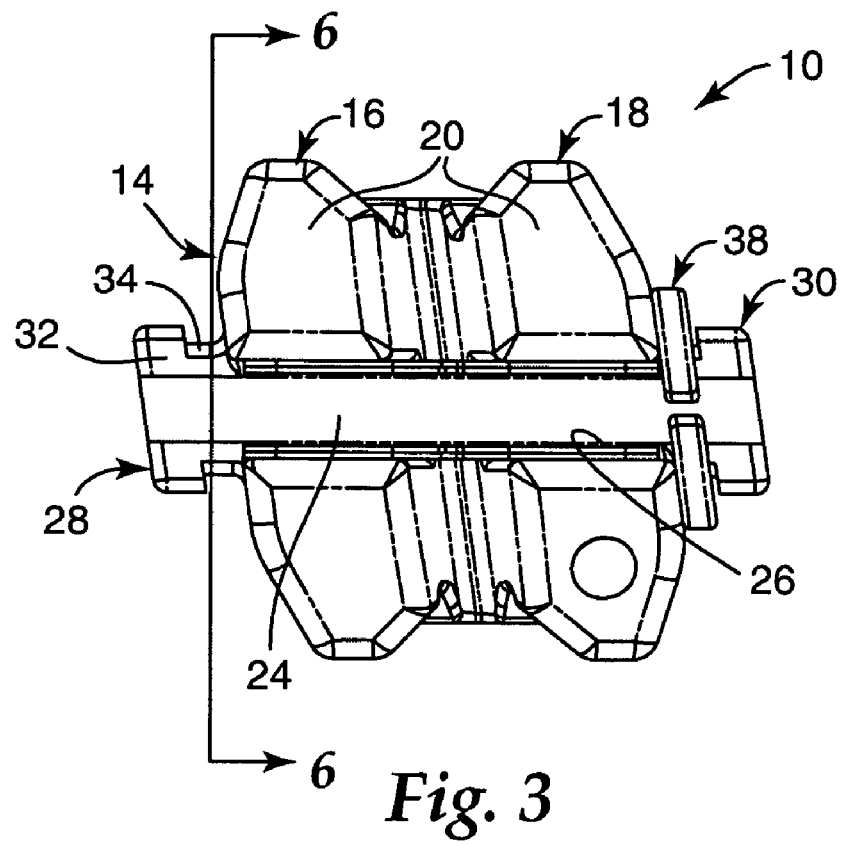
FIG. 3 is an assembled, front elevational view of the appliance shown in FIGS. 1 and 2, looking at the appliance toward its buccolabial side, and wherein one clip of the appliance has been omitted for purposes of illustration.
Figure 4:
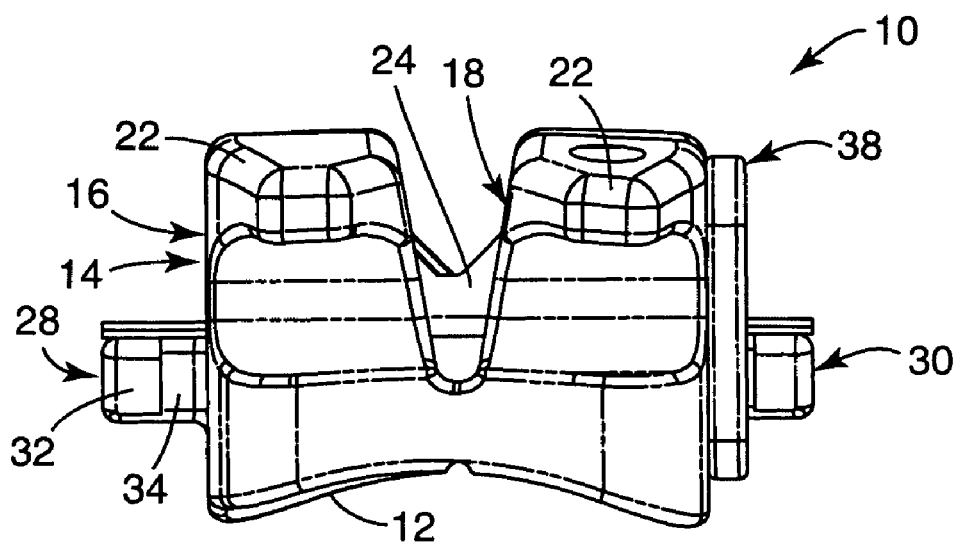
FIG. 4 is a bottom view of the appliance illustrated in FIG. 3, looking at the appliance toward its gingival side.

Preferably, and as shown in FIGS. 1-3, the body 14 (including the body portions 16, 18) is integrally connected to the base 12, and the body 14 and the base 12 form a single, unitary component. However, other constructions are also possible. For example, if the base and the body are made of a metallic material, the base could be manufactured separately from the body and later welded or brazed to the body during an assembly operation.

The appliance 10 also includes an archwire slot liner 24 that is fixed to the body portions 16, 18. The archwire slot liner 24 defines occlusal, gingival and lingual sides of an archwire slot 26. The archwire slot 26 longitudinally extends in a generally mesial-distal direction across the appliance 10, including through a channel of the body portions 16, 18. However, the archwire slot liner 24 is optional and may be omitted. If the archwire slot liner 24 is omitted, the channel of the body portions 16, 18 is made smaller in order to match the cross-sectional area of the archwire and serve as an archwire slot.

The base 12, the body 14 and the archwire slot liner 24 are preferably similar to the corresponding components of the appliances described in U.S. Pat. Nos. 5,439,379 and 5,366,372. Preferably, the base 12 and the body 14 are made of a transparent monocrystalline ceramic material or a translucent polycrystalline ceramic material such as alumina, and the archwire slot liner 24 is made of a metallic material. Examples of suitable materials and methods for constructing the archwire slot liner 24, as well as suitable methods of attaching the archwire slot liner 24 to the body portions 16, 18 are described in U.S. Pat. Nos. 5,358,402 and 5,380,196.

Each of the tiewings 20, 22 extends over a recess or notch for receiving a ligature (not shown). However, the provision of the tiewings 20, 22 and the use of a ligature are optional and may only be needed in certain instances, such as in instances where the tooth is severely malpositioned during the initial stages of treatment. Optionally, the tiewings 20, 22 and the ligature-receiving recesses are constructed as set out in applicant's co-pending U.S. patent application Ser. No. 10/770,779, filed Feb. 3, 2004 and entitled "ORTHODONTIC BRACKET WITH REINFORCED TIEWINGS".

The appliance 10 includes a mesial post 28 and a distal post 30 that are integrally connected to the mesial body portion 16 and the distal body portion 18 respectively. The posts 28, 30 extend outwardly in opposite directions away from each other and from the body 14. Preferably, each post 28, 30 extends along a reference axis that is parallel to the longitudinal axis of the archwire slot 26. As shown for example in FIGS. 4-6, the posts 28, 30 are located in a lingual direction relative to the archwire slot 26.

Figure 6:
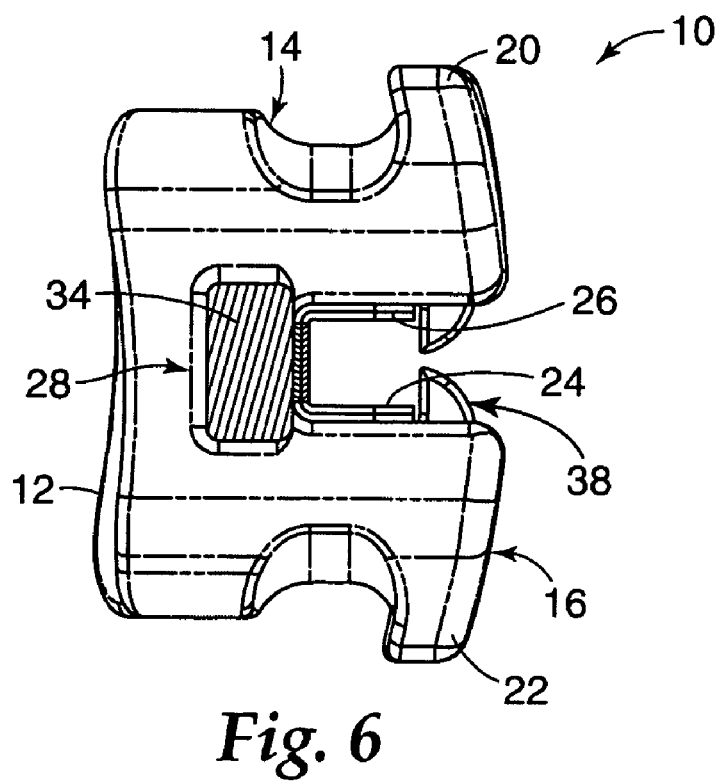
FIG. 6 is a side cross-sectional view taken along lines 6-6 of FIG. 3, showing among other things the configuration of a neck of a post of the appliance.

The mesial post 28 includes an outermost head 32 and a neck 34 that integrally interconnects the head 32 and the mesial body portion 16. As depicted in FIG. 6, the neck 34 has a generally rectangular cross-sectional configuration when considered in reference planes perpendicular to the reference axis along which the post 28 extends or when considered in reference planes generally perpendicular to a mesial-distal axis. Preferably, the occlusal, gingival and lingual sides of the neck 34 in regions along the innermost or distal end of the neck 34 include curved or chamfered sections that are connected to the mesial side of the mesial body portion 16, for enhancing the strength of the connection between the mesial post 28 and the body 14.

Figure 5:
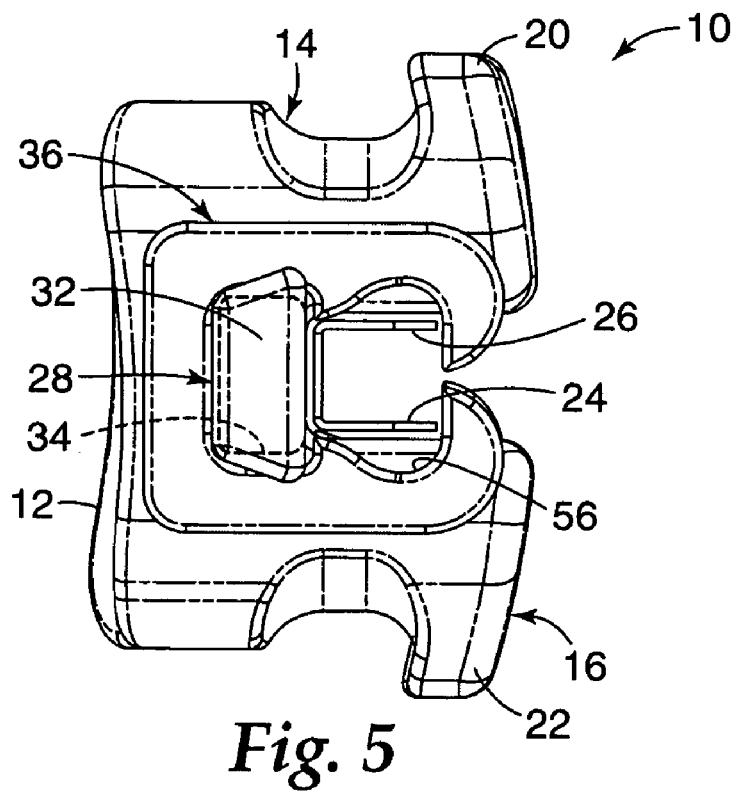
FIG. 5 is a side elevational view of the appliance shown in FIGS. 1-4, looking at the appliance toward its mesial side and illustrating the clip in place.

As shown for example in FIG. 5, the head 32 of the post 28 has a generally trapezoidal configuration when viewed in a distal direction, or when viewed in reference planes that are perpendicular to the reference axis along which the post 28 extends. FIG. 5 also illustrates in dashed lines the cross-sectional shape of the neck 34 for purposes of comparison. As illustrated, the height of the neck 34 and the height of the head 32 are essentially the same along the lingual side of the post 28 when considered in directions along an occlusal-gingival reference axis (i.e. along a vertical axis when viewing FIGS. 5-8). However, along the buccolabial side of the post 28, the height of the head 32 is greater than the height of the neck 34 when considered in directions along an occlusal-gingival reference axis.

The head 32 extends outwardly past the neck 34 a certain distance when considered in reference planes perpendicular to a mesial-distal reference axis or when considered in reference planes perpendicular to the reference axis along which the post 28 extends. In the illustrated embodiment, the head 32 extends outwardly past the neck 34 in at least one, and preferably in both directions along an occlusal-gingival reference axis, or in directions along a vertical axis when viewing FIGS. 5-8. In the illustrated embodiment, this certain distance is determined by adding the distance that the head 32 extends past the neck 34 in an occlusal direction to the distance that the head 32 extends past the neck 34 in a gingival direction. This certain distance decreases as the lingual side of the post 28 is approached and as a third section 46 of the clip 36 (as described below) is approached. This relationship is shown by the dashed lines in FIG. 5 illustrating the occlusal and gingival sides of the neck 34, in comparison to the full lines that depict the occlusal and gingival sides of the head 32. Preferably, this certain distance is zero or approximately zero in regions adjacent the third section 46.

In this embodiment, the archwire slot liner 24 has a rectangular mesial extension that extends over the buccolabial side of the post 28 and is connected to the same by the methods described in U.S. Pat. Nos. 5,358,402 and 5,380,196. However, other constructions are also possible. For example, the archwire slot liner 24 may have a mesial extension that is somewhat "T"-shaped, to match the generally "T"-shaped configuration presented by the neck 34 and the head 32 as depicted in FIG. 3. As yet another option, the mesial extension of the archwire slot liner 24 may be omitted such that the mesial end of the archwire slot liner 28 is flush with the mesial side of the mesial body portion 16.

The appliance 10 also includes a latch for releasably retaining an archwire in the archwire slot 26. In the illustrated embodiment, the latch includes a mesial clip 36 that is connected to the mesial post 28, and a distal clip 38 that is connected to the distal post 30. The mesial clip 36 is omitted from FIGS. 3, 4 and 6 for purposes of illustration.

Figure 7:
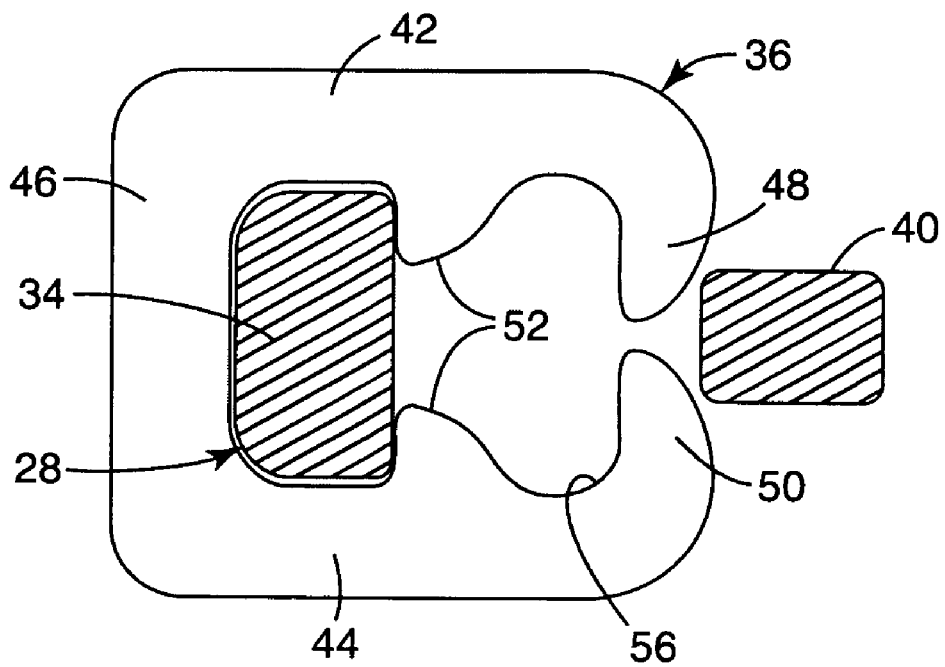
FIG. 7 is a view of the neck and clip alone, along with an exemplary archwire that is about to be received in an archwire slot of the appliance.
Figure 8:
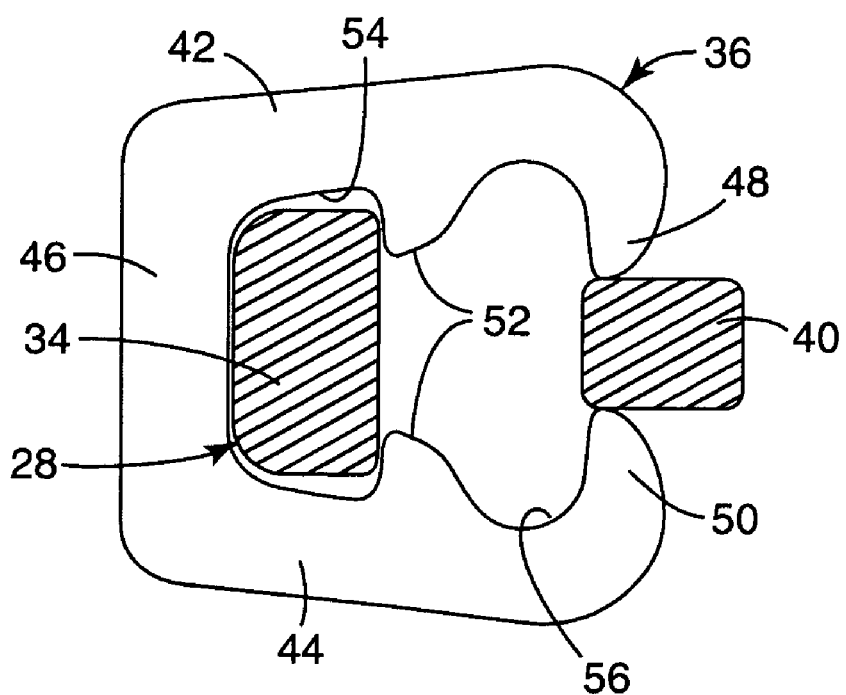
FIG. 8 is a view somewhat similar to FIG. 7 except that the clip is shown in an open position as it might appear during insertion of the archwire into the archwire slot.

The mesial clip 36, the neck 34 and an exemplary archwire 40 are shown alone in FIGS. 7 and 8. The mesial clip 36 includes an elongated occlusal or first section 42, an elongated second or gingival section 44 and an elongated lingual or third section 46. The first and second sections 42, 44 extend in generally parallel directions that lie along a generally buccolabial-lingual reference axis when the clip 36 is relaxed, and the third section 46 extends in a generally occlusal-gingival direction perpendicular to the direction of extension of the sections 42, 44.

The third section 46 also integrally connects the first and second sections 42, 44. Additionally, outer ends of the sections 42, 44 are integrally connected to arm portions 48, 50 respectively. A buccolabial edge of each arm portion 42, 44 is smoothly curved in an arc about a mesial-distal reference axis.

The sections 42, 44, 46 extend along the occlusal, gingival and lingual sides of the neck 34 respectively. In addition, each of the sections 42, 44 includes a somewhat triangular-shaped protrusion that extends along a portion of the buccolabial side of the neck 34. A rear (lingual) portion of the first and second sections 42, 44, along with the third section 46 and the protrusions 52 together at least partially define a recess 54 (FIG. 8) for receiving the neck 34 of the post 28.

A front (buccolabial) portion of the first and second sections 42, 44, along with the arm portions 48, 50 and a portion of the buccolabial side of the neck 34, together at least partially define a region 56 for receiving the archwire 40. As shown for example in FIG. 5, the region 56 is aligned with the archwire slot 26. Overall, the clip 36 presents a generally "C"-shaped configuration when looking in a mesial or distal direction.

The clip 36 is shown in its normal, relaxed orientation in FIGS. 1, 2, 5 and 7. However, the arm portions 48, 50 are movable away from each other in order to admit the archwire 40 into the archwire-receiving region 56 when desired. To this end, the first and second sections 42, 44 deflect outwardly when the clip 36 is opened and bend in respective arcs away from each other in order to enable the arm portions 48, 50 to move apart from each other.

The smooth, outer edge of the arm portions 48, 50 enables the clip 36 to open and admit the archwire 40 into the region 56 by pressing the archwire 40 against the outer curved edges of the arm portions 48, 50. As pressure is exerted by the archwire 40 on the curved edges, the first and second sections 42, 44 deflect away from each other in order to admit the archwire 40 into the region 56. FIG. 8 is an exemplary illustration showing the clip 36 opened, wherein the arm portions 48, 50 have been moved apart from each other a sufficient distance to permit passage of the archwire 40 into the region 56.

As the clip 36 is opened, the protrusions 52 slide across the buccolabial side of the neck 34. However, the protrusions 52 extend inwardly and toward each other a distance sufficient to remain in contact with the buccolabial side of the neck 34 as the clip 36 is opened. As such, the clip 36 remains coupled to the post 28 during such opening movements.

Once the archwire 40 is received in the region 56, the inherent resiliency of the clip 36, and particularly the resiliency of the first and second sections 42, 44, enables the arm portions 48, 50 to spring back toward each other and toward their normal, relaxed configuration as shown in FIGS. 1, 2, 5 and 7 in order to retain the archwire 40 in the archwire slot 26. Preferably, but not necessarily, the region 56 is somewhat larger than the cross-section of the archwire 40 in directions along both an occlusal-gingival reference axis as well as along a buccolabial-lingual reference axis, in order to avoid firm contact between the clip 36 and the archwire 40. The spaces between the clip 36 and the archwire 40 provide what is often referred to as "passive" ligation.

The clip 36 (including the first and second sections 42, 44) is sufficiently stiff to retain the archwire 40 in the archwire slot 26 during the course of treatment so long as the forces exerted by the archwire 40 on the appliance 10 are below a certain minimum value in a generally buccolabial direction (more particularly, in a direction opposite to the direction of insertion of the archwire 40 into the archwire slot 26). However, whenever the forces exerted by the archwire 40 on the appliance 10 in the same direction are greater than the minimum value, as might occur when unexpectedly high forces are encountered, the first and second sections 42, 44 deflect outwardly and the arm portions 48, 50 move apart from each other to open the clip 36 and release the archwire 40 from the archwire slot 26. Further details regarding such forces are described in the aforementioned U.S. Pat. Nos. 6,302,688 and 6,582,226.

Preferably, the clip 36 is substantially identical to the clip 38 and the post 28 is substantially identical in mirror image to the post 30. The latch, comprising the clips 36, 38, preferably releases the archwire 40 from the archwire slot 26 in a generally buccolabial direction whenever the archwire 40 exerts a force in the same direction on the appliance 10 that is in the range of about 0.2 lb (0.1 kg) to about 11 lb (5 kg), more preferably in the range of about 0.4 lb (0.2 kg) to about 5.5 lb (2.5 kg), and most preferably in the range of about 0.75 lb (0.34 kg) to about 3.0 lb (1.4 kg). Preferably, the minimum value is sufficiently high to prevent the archwire from unintentionally releasing from the archwire slot 26 during the normal course of orthodontic treatment. As such, the archwire 40 can exert forces on the appliance 10 sufficient to carry out the treatment program and move the associated teeth as desired.

Preferably, the minimum value for self-release (i.e., self-opening) of the latch is substantially less than the force required in the same direction to debond the appliance 10 from the associated tooth. The minimum value for self-release of the latch is preferably less than about one-half of the force required in the same direction to debond the appliance 10 from the associated tooth. For example, if the expected bond strength of the adhesive bond between the appliance 10 and the associated tooth is 16 lbs (7.2 kg) in a buccolabial direction, the latch is constructed to self-release the archwire 40 whenever the archwire 40 exerts a force in the same buccolabial direction on the appliance 10 that is somewhat greater than about 8 lbs (3.6 kg).

To determine the force to release the latch, a section of archwire is selected having an area in longitudinally transverse sections that is complemental to (i.e., substantially fills) the cross-sectional area of the archwire slot 32. Next, a sling is constructed and is connected to the archwire section at locations closely adjacent, but not in contact with the heads of the posts 28, 30 including the head 32. Optionally, the sling is welded or brazed to the archwire section. Next, the sling is pulled away from the appliance 10 while the appliance 10 is held in a stationary position, taking care to ensure that the longitudinal axis of the archwire section does not tip relative to the longitudinal axis of the archwire slot 26. The force to release the latch may be determined by use of an Instron testing apparatus connected to the sling, using a crosshead speed of 0.5 in/min (1.3 cm/min). Alternatively, a shaker apparatus (such as Model 300 from APS Dynamics of Carlsbad, Calif.) may be used along with a force transducer (such as model 208C01 from PCB of Buffalo, N.Y.) to measure the force.

Preferably, the distance between the opposed ends of the arm portions 48, 50 is less than the overall occlusal-gingival dimension of the smallest archwire 40 expected to be used during the course of treatment. The archwire 40 need not fill the archwire slot 26 and flatly engage the wall portions defining the archwire slot 26 in all instances. For example, a somewhat smaller wire, and perhaps an archwire 40 having a circular cross-sectional shape, may be used during a portion of the treatment program. The distance between the opposed ends of the arm portions 48, 50 is preferably selected so that a variety of archwires of different cross-sectional configurations may be used in connection with the appliance 10.

Preferably, and as mentioned above, the distal clip 38 is substantially identical to the mesial clip 36. Optionally, however, it is possible to construct the clips 36, 38 somewhat differently to address certain circumstances. For example, if a malpositioned tooth is initially oriented such that its mesial side is rotated in a lingual direction, it may be desirable to increase the stiffness of the mesial clip 36 so that a somewhat greater force is needed to release the archwire 40 from the archwire slot 26 in comparison to the force needed to release the archwire 40 from the distal clip 38. Other options are also possible.

Optionally, the spring clips 36, 38 are cut from a flat section of metallic stock material. Suitable metallic materials include shape memory alloys such as alloys of nitinol and beta-titanium. The clips 36, 38 may be cut from the stock material using a stamping, die cutting, chemical etching, EDM (electrical discharge machining), laser cutting or water jet cutting process. As another option, the clips 36, 38 could be formed and then heat-treated to set their shapes.

As presently preferred, the clips 36, 38 are made from flat annealed superelastic material (such as nitinol) having a pickled surface. Preferred nitinol materials have a nickel content of 55.97% by weight and an $A_f$ of 10°±5° C. The nitinol is cold worked to 37.5% and has a thickness in the range of about 0.012 in. (0.3 mm) to about 0.016 in. (0.4 mm). The clips 36, 38 are first cut in a rough cutting EDM process, then cut along their edges for an additional one or more times using an EDM process in order to smooth the edges.

Alternatively, a laser cutting process or chemical etching process could be used to make the clips 36, 38. Preferably, the clips 36, 38 are constructed so that the longitudinal direction of the clip material, or the principal direction of grain flow of the clip material, is substantially parallel to the direction of extension of the first and second sections 42, 44 (i.e. a generally buccolabial direction in the illustrated embodiment).

Subsequent to the EDM, laser cutting or chemical etching process, the clips 36, 38 are tumbled in order to further round their edges. An example of a suitable tumbling machine is model LC-600-2+2 from Richwood Industries. Using a small barrel, and a machine speed of 200 rpm, the clips are tumbled for about 2 hours in 500 cc of water and tumbling media. An example of suitable tumbling media is a mixture of 500 cc of ceramic media (shaped ACC, type M, size $^3/_{16} \times ^3/_8$ (4.7 mm×9.5 mm)), 25 cc of white alumina powder no. 40, and 25 cc of soap powder compound no. 43, all from Richwood Industries. The tumbled clips are then polished for one-half hour in an ultrasonic screen barrel in a tank of solution. An example of a suitable solution is 3 liters of deionized water, 3 liters of pickling solution and 0.6 liter of hydrogen peroxide. A suitable pickling solution is No. TI121 Pickling Solution from Aya International of Los Angeles, Calif.

Other optional aspects of the clips 36, 38 are described in applicant's published U.S. patent application entitled "ORTHODONTIC APPLIANCE WITH FATIGUE-RESISTANT ARCHWIRE RETAINING LATCH"; No. 2004/0086825, published May 18, 2004.

During manufacture of the appliance 10, the archwire slot liner 24 is affixed to the body 14 and the clips 36, 38 are then assembled to the posts 28, 30 respectively. To connect the clip 36 to the post 28, the clip 36 is opened by moving the sections 42, 44 in directions away from each other a distance sufficient to clear the head 32 and enable the neck 34 to be received in the recess 54 by moving the clip 36 in a distal direction. Next, pressure on the sections 42, 44 is relieved and the clip 36 springs back to its normal, relaxed configuration such as shown in FIGS. 1, 2, 5 and 7, whereupon it is held in place by the head 32.

The present invention provides significant advantages during manufacture and assembly of the appliance 10. In particular, the relationship between the configuration of the head 32 and the neck 34 provides a substantial benefit, in that the extent to which the sections 42, 44 must be moved apart from each other to clear the head 32 is reduced in comparison to what might otherwise be necessary. As a result, the stresses that might be otherwise imposed on the clip 36 are substantially reduced when the clip 36 is opened to clear the head 32 and be installed on the post 28. The reduction in stress on the clip 36 as described above helps to ensure that the fatigue life of the clip is not unduly compromised. As a result, the clip 36 is unlikely to fracture during the course of treatment, even though the clip 36 may be opened and closed a number of times.

The present invention also advantageously enables the appliance to be constructed with a base having flanges that extend in mesial and distal directions past the appliance body. Although such flanges are not shown in the illustrated embodiment, they are sometimes desired in order to increase the surface area of the base and hence the strength of the adhesive bond between the appliance and the patient's tooth, especially when the appliance body is made of a metallic material. In the past, the clips of the "SMARTCLIP" brand appliances mentioned above were assembled to the posts by moving the clips toward the neck in a reference plane perpendicular to the neck to avoid spreading open the clips to an undue extent, and such an assembly method would be rendered difficult or impossible in instances where the appliance base included flanges.

Additionally, the invention enables the posts 28, 30, and particularly the neck of the posts 28, 30 to be somewhat larger than might otherwise be practical. As such, the likelihood of the posts 28, 30 fracturing and detaching from the body 14 is substantially reduced. This aspect is particularly advantageous when the body 14 is made of a material that has relatively little ductility or has relatively little strength in tension such as a ceramic material.

A number of other constructions are also possible. For example, the body and/or base may be made of a metallic (such as stainless steel) or plastic material (such as fiber-reinforced polycarbonate) instead of the ceramic materials mentioned above. Furthermore, the archwire slot liner 24 is optional and may be omitted if desired.

All of the patents and patent applications mentioned above are hereby expressly incorporated by reference herein. The embodiments described in detail above and shown in the drawings are intended to exemplify the invention, and should not be deemed to limit the scope of the claims that follow.

The invention claimed is:

1. An orthodontic appliance comprising:
a base;
a body extending outwardly from the base;
an archwire slot extending across the appliance in a generally mesial-distal direction;
a latch for releasably retaining an archwire in the archwire slot, wherein the latch comprises a clip with a region next to the archwire slot for receiving an archwire, wherein the clip includes a first section, a second section and a third section interconnecting the first section and the second section, wherein the first section and the second section are movable away from each other to admit an archwire into the region, and wherein the clip also includes a recess at least partially defined by the first section, the second and the third section; and
a post extending outwardly from the body along a reference axis and into the recess for coupling the clip to the body, the post including an outermost head and a neck interconnecting the head and the body, wherein the head extends outwardly past the neck a certain distance when considered in reference planes perpendicular to the reference axis, wherein the certain distance decreases as the third section of the clip is approached and wherein the first section and the second section are movable away from each other a distance sufficient to clear the head and enable the clip to be coupled to the body while moving the clip in a direction parallel to the archwire slot.

2. An orthodontic appliance according to claim 1 wherein at least one of the first section and the second section is movable for admitting the post into the recess.

3. An orthodontic appliance according to claim 1 wherein the first section and the second section are both relatively movable in directions away from each other for admitting the post into the recess.

4. An orthodontic appliance according to claim 1 wherein the neck has a generally rectangular configuration when viewed in a direction along the reference axis.

5. An orthodontic appliance according to claim 1 wherein the head has a generally trapezoidal configuration when viewed in a direction along the reference axis.

6. An orthodontic appliance according to claim 1 wherein the third section is remote from the archwire slot.

7. An orthodontic appliance according to claim 1 wherein the third section is adjacent the base.

8. An orthodontic appliance according to claim 1 wherein the third section has a height that is approximately equal to the height of the neck when considered in directions along an occlusal-gingival reference axis.

9. An orthodontic appliance according to claim 1 wherein the head and the neck have approximately the same overall width when considered in directions along a buccolabial-lingual reference axis.

10. An orthodontic appliance according to claim 1 wherein the neck and the head have approximately equal heights in regions next to the third section when considered in directions along an occlusal-gingival reference axis.

* * * * *